United States Patent [19]

Heineck

[11] Patent Number: 5,515,158

[45] Date of Patent: May 7, 1996

[54] RETROREFLECTION FOCUSING SCHLIEREN SYSTEM

[75] Inventor: James T. Heineck, San Jose, Calif.

[73] Assignee: The United States of America as Represented by the Administrator of the National Aeronautics and Space Administration, Washington, D.C.

[21] Appl. No.: 189,258

[22] Filed: Feb. 1, 1994

[51] Int. Cl.$^6$ ................................. G01N 21/41
[52] U.S. Cl. ....................................... 356/129
[58] Field of Search ................... 356/129, 73, 361, 356/362, 359, 128, 237, 445; 250/237 G; 73/147, DIG. 1, 800

[56] References Cited

U.S. PATENT DOCUMENTS

| | | | |
|---|---|---|---|
| 2,977,847 | 4/1961 | Meyer-Arendt | 356/129 |
| 3,468,610 | 9/1969 | Muffoletto | 356/129 |
| 3,540,829 | 11/1970 | Collinson et al. | 356/129 |
| 3,617,130 | 11/1971 | Kelley et al. | 356/129 |
| 4,139,291 | 2/1979 | Parthasarathy | 356/129 |
| 4,188,117 | 2/1980 | Yamauchi et al. | 356/237 |
| 4,283,147 | 8/1981 | Dreyfus et al. | 356/445 |
| 4,854,708 | 8/1989 | Kafri et al. | 356/73 |
| 4,907,888 | 3/1990 | Clarke et al. | 356/371 |
| 4,920,385 | 4/1990 | Clarke et al. | 356/446 |
| 4,930,893 | 6/1990 | Manian | 356/344 |
| 4,979,820 | 12/1990 | Shakkottai et al. | 356/129 |

FOREIGN PATENT DOCUMENTS 0746260   7/1980   U.S.S.R. ............................. 356/129

OTHER PUBLICATIONS

"Selected Papers on Schlieren Optics", SPIE Milestone Series, vol. MS 61, Brian J. Thompson, General Editor.
"Principles on Guided Missile Design", edited by Grayson Merrill, Captain, U.S.N.(Ret.), p. 547.
McGraw-Hill Encyclopedia of Science & Technology 16, SAB-SON, 7th Edition, pp. 109, 400-401.
"An Improved Large-Field Focusing Schlieren System", 29th Aerospace Sciences Meeting, Jan. 7-10, 1991, Reno, Nevada, AIAA 91-0567, Leonard M. Weinstein, NASA-Langley, Hampton, VA.

Primary Examiner—Hoa G. Pham
Attorney, Agent, or Firm—Kenneth L. Warsh; Guy Miller

[57] ABSTRACT

A retroreflective type focusing schlieren system which permits the light source to be positioned on the optic side of the system. The system includes an extended light source, as opposed to a point source, located adjacent a beam splitter which projects light through the flow field onto a reflecting grating in the form of a grid which generates sheets of light that are directed back through the flow field and the beam splitter onto a primary lens behind which is located a cut-off grid having a grid pattern which corresponds to the grid pattern of the reflecting grating. The cut-off grid is adjustably positioned behind the primary lens and an image plane for imaging the turbulence is adjustably located behind the cut-off grid.

9 Claims, 3 Drawing Sheets

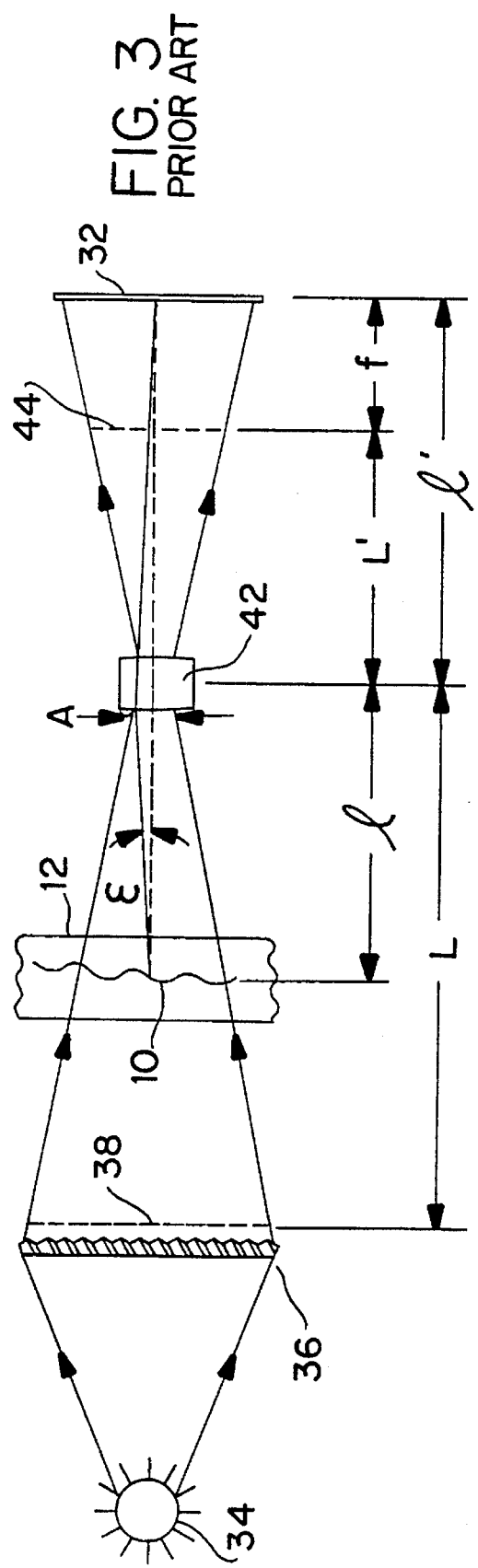
FIG. 3
PRIOR ART
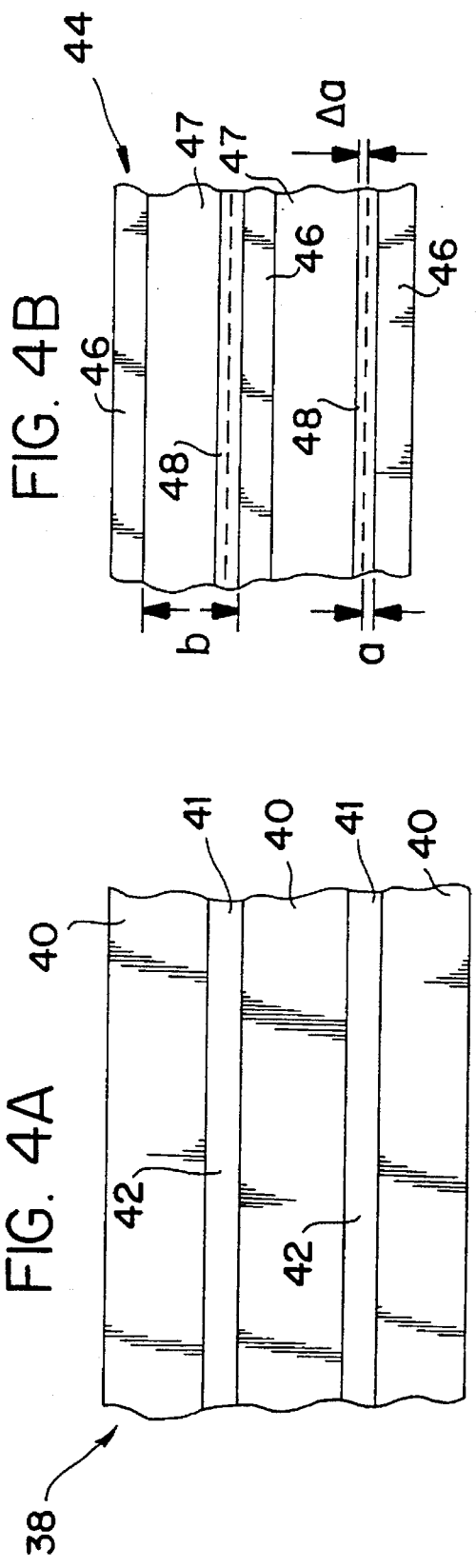
FIG. 4B
FIG. 4A

RETROREFLECTION FOCUSING SCHLIEREN SYSTEM

This invention was made by an employee of the U.S. Government and therefore may be used by and for the Government for governmental purposes without the payment of any royalty thereon or therefor.

BACKGROUND OF THE INVENTION

1. Field of the Invention

This invention relates generally to schlieren type apparatus for monitoring turbulent flow and more particularly to focusing type schlieren apparatus.

2. Description of the Prior Art

Refraction anomalies produced in transmitted light by differences in density or other anisotropy in parcels or strata of air or other fluids are known as schlieren. Natural scintillation phenomena in the atmosphere results from density schlieren developed by turbulent processes. Schlieren apparatus is generally known and is commonly used for observing and photographing refractive index gradients which occur, for example, in the study of air flow in wind tunnels.

In its simplest configuration, apparatus for observing schlieren involves placing a pair of lens on either side of a flow field with a point light source being located at the focal point of one of the lenses. The lens adjacent the light source collimates the light emanating therefrom which is refracted as it passes through the medium of the flow field. The lens on the other side of the flow field acts as a collective lens which, if matched with the other lens, focuses the light leaving the flow field to a point and should match the size and shape of the light source. When a knife edge is placed at the second focal point in such a way to cut the light point in half, it has the effect of darkening the background from a bright white to an even gray. The knife edge then blocks light refracted in that direction showing the gradient as dark. Light refracted in the opposite direction shows up brighter against the background. The image of the turbulence in the flow field can then be viewed visually either on some type of screen or photographically on film or video.

Such schlieren systems are expensive, requiring a highly specialized light source and require a large amount of space on both sides of the flow field.

This type of apparatus has evolved into focusing schlieren systems which remove the requirement for collimated light to display density gradients and involves utilizing "sheets of light" which are generated by back lighting a high contrast grid pattern. The sheets of light are directed through the flow field onto a lens that projects the image of the grid to a focal plane where there is located a negative of the high contrast photographic grid pattern whose dark lines each act as knife edges. This element is known as a cut-off grid.

Accordingly, as the light sheets pass through the turbulence of the flow field, the sheets of light refract and are either stopped by the "knife edges" of the cut-off grid, or pass through the space therebetween and the image of the turbulence is projected through the knife edges where it can then be viewed or captured as before.

Focusing schlieren systems normally require substantial space on both sides of the test section for the lighting/grid portion and the optic/image components.

Focusing schlieren type systems are discussed in detail in a publication entitled "An Improved Large-Field Focusing Schlieren System", Leonard M. Weinstein, AIAA 91-0657, 29th Aerospace Science Meeting, Jan. 7–10, 1991, pp. 1–12. Portions of this publication comprise prior art which is recognized in the accompanying detailed description of the subject invention.

SUMMARY

Accordingly, it is an object of the present invention to provide an improvement in schlieren apparatus.

It is a further object of the invention to provide an improvement in focusing type schlieren apparatus for imaging fluid turbulence in a flow field where space is restricted.

It is still another object of the invention to provide an improved focusing type schlieren apparatus which permits the observation of turbulence in environments which afford only a single viewing port in a test section.

And it is still a further object of the invention to generate schlieren fields large enough for imaging fluid turbulence in connection with full scale models in both an interior and exterior environment.

The foregoing and other objects and advantages of the subject invention are realized by a retroreflective type focusing schlieren system which permits the light source to be positioned on the optic side of the system and comprises an extended light source, as opposed to a point source, located adjacent a beam splitter which projects light through the flow field onto a reflecting grating which generates sheets of light that are directed back through the flow field and the beam splitter onto a primary lens behind which is located a cut-off grid having a grid pattern which corresponds to the grid pattern of the reflecting grating. The cut-off grid is adjustably positioned behind the primary lens and an image plane for imaging the turbulence is adjustably located behind the cut-off grid.

BRIEF DESCRIPTION OF THE DRAWINGS

The following detailed description of the invention will be more readily understood when considered in conjunction with the accompanying drawings wherein:

FIG. 3 is a mechanical schematic diagram illustrating the focusing type schlieren system;

FIGS. 4A and 4B are partial views generally illustrative of the source grid and cut-off grid, respectively, utilized in the focusing schlieren system shown in FIG. 3.

DETAILED DESCRIPTION OF THE INVENTION

Figure 1:
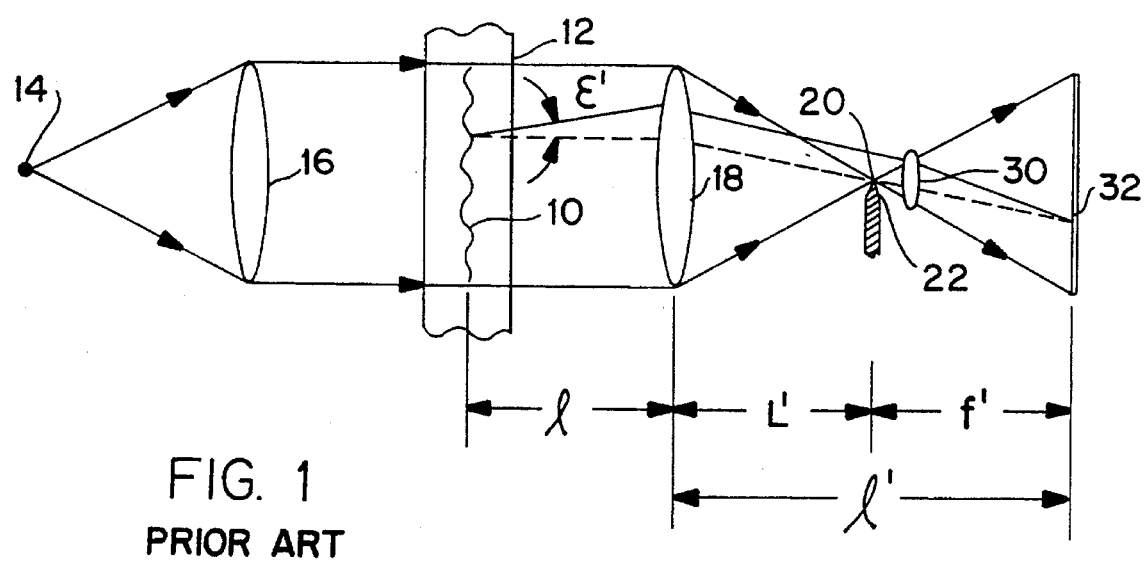
FIG. 1 is a mechanical schematic diagram illustrating a conventional schlieren system for viewing turbulence in a flow field.
Figure 2:
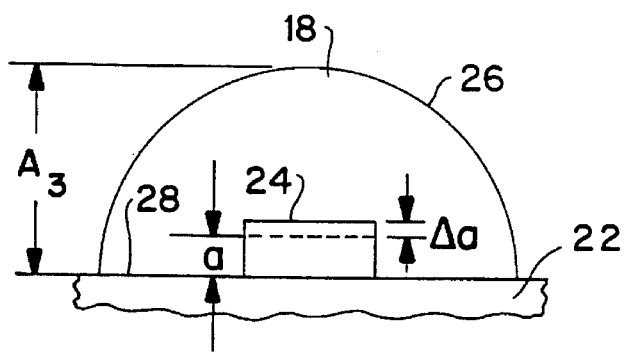
FIG. 2 is a diagram illustrative of schlieren imaging in the system shown in FIG. 1.

Referring now to the drawings, wherein like reference numerals refer to like parts, and more particularly to FIGS. 1 and 2, illustrated thereat is a conventional schlieren system utilized for imaging fluid turbulence in a flow field 10 within a test section 12 without introducing dyes, smoke or seed into the fluid.

As shown in FIG. 1, a conventional schlieren system starts with a point source of light 14 which is placed at the focal point of a lens 16 located between the light source 14 and the flow field 10. When placed at the focal point of the lens 16, the light emanating from the point source 14 becomes collimated or parallel. The parallel light passes through the flow field 10 where it is refracted as it passes through the density variations of the medium including the turbulence to be monitored. The angle change due to refraction in the flow field 10 is denoted by $\epsilon'$ in FIG. 1.

On the output side of the system, there is located a second lens 18 which matches the lens 16 on the input side. The lens 18 operates to focus the collimated beam leaving the test section 12 to a point 20 which substantially matches the size and shape of the light source 14. The distances l and L' denote the distance from the turbulence in the flow field 10 to the lens 18 and from the lens 18 to the focal point 20, respectively.

At the focal point 20, there is located a member which includes a knife edge 22 that acts to intersect the light impinging at the focal point 20. The knife edge 22 is placed transverse to the light so as to cut the light impinging on the focus 20 in half. This has the effect of darkening the background from a bright white to an even gray. The knife edge 22 blocks light refracted in the plane of the knife edge providing a dark image of the gradient. For light refracted in the opposite direction, it shows brighter against the gray background.

This is depicted in FIG. 2 where reference numeral 24 represents the image of the light source 14 appearing at the knife edge 22. The dimension $A_3$ is the distance above the knife edge 22 to the peripheral edge 26 of the lens 18. Reference character a denotes the light source image height above the edge or cut-off line 28 of the knife edge 22 while $\Delta a$ represents the change in the image height due to refraction.

Further as shown in FIG. 1, a third lens 30 is located behind the knife edge member 22 for projecting the schlieren image on an image plane 32 where there is placed means for capturing the image which may be, for example, a ground glass plate, photographic film, or a video camera, not shown. The dimensions f' and l' represent the distances from the cut-off at the knife edge 22 to the image plane 32 and the distance from the second lens 18 to the image plane 32.

Referring now to FIG. 3, shown thereat is a diagram which is illustrative of a typical focusing schlieren system. A focusing schlieren system does not require collimated light to generate an image of the density gradients, but includes apparatus for generating "sheets of light" that are refracted by the density gradients of the turbulence in the flow field 10. These sheets of light, not shown, are generated by back lighting a high contrast grid pattern by an extended, i.e. a non point, source of light 34. The grid pattern is produced by a Fresnel field lens 36 in front of which is placed a grid member 38. The grid member 38 is commonly known as a source grid. The source grid 38 can be fabricated, for example, photographically by forming a Ronchi ruling on a high contrast film.

A typical example of a source grid is shown in FIG. 4A where a plurality of generally horizontal light blocking rulings 40 are spaced apart to provide a plurality of mutually parallel horizontal slits 41 from which "sheets of light" emanate. The grid pattern of light passing through the flow field 10 is refracted by the turbulence as shown by the angle $\epsilon$, where it impinges on a primary optic device 42 which may be, for example, a camera lens. The dimension A denotes the clear aperture of the lens 42 which comprises a focusing lens, with the distance l being either fixed or variable, depending upon the particular application.

On the other side of the camera lens 42 located at a distance L' is a second or cut-off grid 44. The cut-off grid 44 is formed by means of making a relatively high contrast photographic negative of the source grid 38 to develop a configuration such as shown in FIG. 4B including a plurality of horizontal opaque lines 46 which are separated by spaces 47 having a distance b and which act as a plurality of knife edges 48 as opposed to a single knife edge 22 shown in FIG. 1 of a conventional schlieren system.

As depicted in FIG. 4B, each line 46 generates a schlieren image of a respective sheet of light coming from the slits 42 of the source grid 38, with the image thereof being illustrated by reference numeral 48. As shown, the dimension a represents the light source image height above the cut-off edge 48 of the opaque line 46, while the dimension $\Delta a$ is indicative of the change in the dimension a due to refraction of the light sheets through the flow field turbulence 10.

Figure 5:
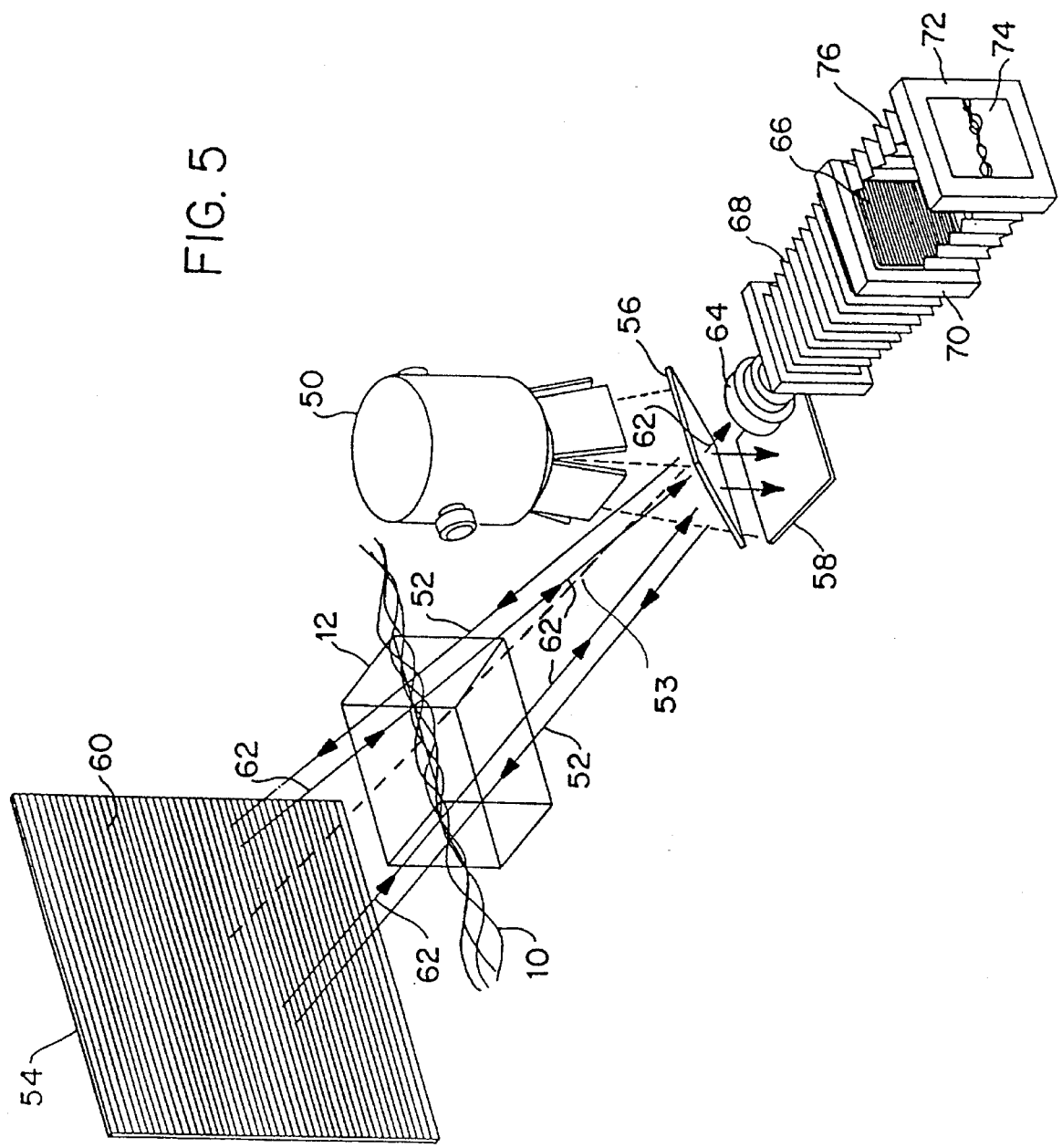
FIG. 5 is a perspective view illustrative of the preferred embodiment of the subject invention.

Referring now to FIG. 5, shown thereat is the preferred embodiment of the invention which comprises a retroreflective focused schlieren imaging system which permits relatively large schlieren fields to be created while positioning the light source on the optic side of the system so that only a single viewing port in a test section 12 need be provided.

As illustrated, an extended, i.e. relatively large light source 50 is located at an angle of 90° with respect to a beam of light 52 which is projected along a central primary optical axis 53 through a test section 12 including a flow field 10 onto a reflecting grating 54. This is achieved by placing a beam splitter 56 directly beneath the light source 50. A light absorber element 58 is also placed below beam splitter 56 in line with the light source 50.

The grating 52 includes a retroreflective surface 60 having a carefully constructed grid pattern which operate to form "sheets of light" from the light beam 52. The sheets of light return as shown by reference numeral 62 back through the turbulence of the flow field 10 where the refracted light is directed to a primary lens 64 which may be, for example, a camera lens. Directly behind the lens 64 is a cut-off grid 66 which can be adjustably positioned relative thereto. A bellows 68 is utilized, for example, between the lens 64 and the cut-off grid 66 to exclude any extraneous light. The optical system, being adjustable, can selectively focus on the region of turbulence in the flow field 10 of most interest. The distortions outside the region of interest, such as windows or other distracting turbulence within the test section can be negated. The cut-off grid 66 again is formed to include a grid pattern 70 corresponding to the grid pattern 60 of the retroreflective grating 54. Further as shown in FIG. 5, an imaging plane 72 including an imaging plate or some such apparatus 74 for viewing the schlieren is located behind the cut-off grid 66 and includes additional light excluding means which may be, for example, a second bellows member 76. When desired, the extended light source 50 may simply be configured by means of a ring light, not shown, located around the primary optic member i.e. the lens 64.

Such a system as shown in FIG. 5 has an advantage in that the system will remain "in tune" indefinitely irrespective of the changes in the light source or image gathering apparatus. This provides a distinct advantage over a laser type of system where the fringe pattern will have a tendency to drift, requiring the laser to be periodically tuned.

Thus what has been shown and described is a retroreflective focusing schlieren system which permits the use of any type of light source and allows for versatility not capable of being achieved by known prior art focusing schlieren systems.

Having thus shown and described what is at present considered to be the preferred embodiment of the invention, it should be noted that the same has been made by way of illustration and not limitation. Accordingly, all modifications, alterations and changes coming within the spirit and scope of the invention as set forth in the appended claims are herein meant to be included.

I claim:

1. Retroreflective focusing schlieren apparatus, comprising:

a light source located on an optic side of a test section including a flow field and being oriented so as to intersect a central primary optical axis passing through said test section at a predetermined angle;

a gridded retroreflector aligned with the primary optical axis and being located on the other side of the test section opposite the flow field and including a grid pattern formed on a front surface of said retroreflector for generating sheets of light which emanate therefrom when receiving light from said light source;

means located adjacent the light source on the optic side of the test section and being aligned with the primary optical axis for directing light from the light source through the flow field to the retroreflector;

lens means aligned with the optical axis and being located on the optic side of the test section for receiving said sheets of light from said retroreflector following refraction after passing through said flow field;

cut-off means comprising a cut-off grid, having a grid pattern corresponding to the grid pattern on the front surface of said retroreflector, located behind said lens means for intersecting said sheets of light and generating images of schlieren in the flow field;

means located adjacent said cut-off means for viewing said images of schlieren.

2. The apparatus as defined by claim 1 wherein said light source comprises an extended light source for generating large schlieren fields of turbulence in the flow field.

3. The apparatus as defined by claim 2 wherein said means for directing light from the light source to the retroreflector comprises a beam splitter.

4. The apparatus as defined by claim 3 wherein the light source intersects said central primary axis at an angle of substantially 90° and facing said beam splitter.

5. The apparatus as defined by claim 4 and additionally including light absorbing means located beneath the beam splitter for absorbing light passing from the light source through the beam splitter.

6. The apparatus as defined by claim 3 wherein said lens means comprises a camera type lens located between the beam splitter and said cut-off means.

7. The apparatus as defined by claim 1 and additionally including means for excluding external light between said lens means and said cut-off means.

8. The apparatus as defined by claim 1 wherein said means for viewing said images of schlieren include a planar viewing surface positioned behind said cut-off means.

9. The apparatus as defined by claim 8 and additionally including means for excluding external light between said cut-off means and said planar viewing surface.

* * * * *